United States Patent
McDowell (10) Patent No.: US 6,171,340 B1
(45) Date of Patent: Jan. 9, 2001

(54) METHOD AND DEVICE FOR REGENERATING CARTILAGE IN ARTICULATING JOINTS

(76) Inventor: Charles L. McDowell, 6425 Roselawn Rd., Richmond, VA (US) 23226

( * ) Notice: Under 35 U.S.C. 154(b), the term of this patent shall be extended for 0 days.

(21) Appl. No.: 09/256,006

(22) Filed: Feb. 23, 1999

Related U.S. Application Data (63) Continuation-in-part of application No. 09/104,657, filed on Jun. 25, 1998.
(60) Provisional application No. 60/076,253, filed on Feb. 27, 1998.

(51) Int. Cl.[7] ............... A61F 2/30; A61F 2/40; A61F 2/38; A61B 17/56
(52) U.S. Cl. .................. 623/18.11; 623/19.11; 623/902; 623/20.14
(58) Field of Search .................. 623/18–23, 902, 623/18.11, 19.11

(56) References Cited

U.S. PATENT DOCUMENTS

| | | | |
|---|---|---|---|
| 4,385,404 | * 5/1983 | Sully et al. | 128/898 |
| 5,108,441 | * 4/1992 | McDowell | 623/19 |
| 5,624,463 | 4/1997 | Stone et al. . | |
| 5,632,745 | 5/1997 | Schwartz . | |
| 5,723,331 | 3/1998 | Tubo et al. . | |
| 5,769,899 | 6/1998 | Schwartz et al. . | |
| 5,846,931 | 12/1998 | Hattersley et al. . | |
| 5,866,415 | 2/1999 | Villeneuve . | |

* cited by examiner

Primary Examiner—V Millin
Assistant Examiner—Choon P. Koh
(74) Attorney, Agent, or Firm—Susan L. Firestone; Paul W. O'Malley (57) ABSTRACT

A method of repairing a damaged joint uses a prosthetic shield and/or spacers to protect regenerating cell growth on the articulating surface of the joint. The shield and spacers protect the articulating surfaces of the joint from compression and frictional stresses while guarding the bone from further damage. The shield and spacers also can deliver transplanted cells and cell enhancing growth factors to the site. The shield can be left in place or removed after the joint heals.

13 Claims, 4 Drawing Sheets

METHOD AND DEVICE FOR REGENERATING CARTILAGE IN ARTICULATING JOINTS

CROSS REFERENCE TO RELATED APPLICATION

This application is a continuation-in-part application of U.S. patent application Ser. No. 09/104,657 filed Jun. 25, 1998, which claimed the benefit of U.S. provisional application Ser. No. 60/076,253, filed Feb. 27, 1998.

BACKGROUND OF THE INVENTION

1. Field of the Invention

The present invention relates to a method and related devices used to regenerate cartilage in articulating joints.

2. Description of the Prior Art

The skeleton has specialized joints for different types of movement. Joints have two or more bones that articulate with respect to each other. Joints extend and flex as hinges like the fingers. They rotate like the ball within the socket of the hip.

The bones of a healthy joint are not actually seated against one another during movement. A layer of articular cartilage usually separates joint bones. Articular cartilage decreases the stress on the bones during motion and subsequently the wear and tear of the bone over a lifetime of movement.

Both friction and compression are often present during movement. Walking upright, for example, places both compressive and frictional stress on the hip. The weight of the upper body pushes down on the joint while the leg rotates within the hip.

Frictional stress is due to the relative movement of two objects. In this case, bone moving against bone generates a great deal more frictional stress than is the case when articular cartilage is present. Without articular cartilage, the surfaces of the bones are exposed, friction increases and movement becomes more difficult. If the bone is covered with cartilage, the bones smoothly glide on the cartilage and movement is easier. By reducing friction, articular cartilage eases movement.

Bones of the joint are not only stressed by movement and friction. Articular cartilage cushions bones against compression. Compressive stress compresses bones by the pressure of bone against bone, such as the weight of the body pushing against the bone or the force of one bone pushing against another.

Disease and injury damage articular cartilage. Osteoarthritis, chondromalacia and rheumatoid arthritis erode the cartilage from the joint. Injuries such as bone fractures can tear or bruise the cartilage, which can also lead to cartilage loss.

The loss of articular cartilage increases friction and compression during movement. The remaining articular cartilage rapidly degenerates under these stresses which causes the bones of the joints to touch against one another directly. The movement of exposed bone against bone further degenerates the articulating surfaces of the bones in the joint to decrease mobility and increase pain.

Repairing damaged joints may require joint replacement. Surgical repair of the damaged joints, such as hip replacement with a prosthesis, is a major operation. Surgical replacement, especially of large joints, is painful and traumatic, often resulting in substantial blood loss and requiring a lengthy recovery period. Furthermore, surgical replacement often requires the surgeon to strip away the cartilage attached to any remaining bone to properly insert and fit the prosthesis. This leaves the joint with little if any remaining articular cartilage.

The cells of native articular cartilage do not regrow in situ. However, if the damaged cartilage is removed and the bone is wounded, such as by grinding, the joint reheals. The wounded bone serves as a source of stem cells, such as endothelial cells and other pleuripotential cells, and chondroblasts. The stem cells grow out of the wounded bone and produce a layer of cartilage. This newly grown cartilage serves to protect the joint bones from friction and compression, much like native articular cartilage does.

Alternatively, stem cells can be transplanted to the joint. These stem cells can be harvested either in vitro from cell culture or in vivo from other parts of the patient's or donor's body. In addition, growth and attachment factors can be delivered to the joint by attaching them to a scaffolding or matrix attached to the joint.

Whether from wounded bone or transplantation, fragile stem cells subjected to compressive or frictional stresses do not grow and form a layer of cartilage. The stresses placed on the growing cells at the surface are great, comparable to growing cells under a moving rock that scrapes and grinds.

The prior art does not adequately address the problems of protecting the stem cells from compressive and frictional stress. A hip replacement, for example, replaces the damaged femoral head and reams the acetabulum to fit the new femoral prosthesis. The prosthetic femoral head directly contacts and rubs against the raw acetabulum with each movement.

Prior art protective caps inadequately protect delicate stem cells. These caps provide a smoother surface which reduces friction during movement. This reduction of friction is decreased, however, whenever the bones move against any irregularity in the surface of the bone, such as peaks or valleys. Furthermore, the caps have little effect on the reduction of compression. The force of bone against bone still bears directly on the stem cells.

Therefore, there are a number of objects of the invention. One object of the invention is to shield the surface of the bone to decrease the compression and frictional stresses and aid in the regeneration of cartilage. The invention provides a protected surface for stem cells, as well as grafted cells and transplanted materials to attach and grow, such as fibroblasts, chondroblasts, fetal tissue, periosteum, cartilage and artificial cartilaginous-like materials.

Another object of the invention is to repair the joint without requiring joint replacement.

Another object of the invention is to provide access to stem cells directly from the bone.

Another object of the invention is to deliver cells and cartilage growth enhancing factors to the site. Cells can be transplanted along with any desired growth and/or attachment factors and delivered to the joint by attaching them to the shield and/or spacers of the invention. The shield and spacers can also be used to attach and maintain scaffolding material carrying transplanted cells or factors to the joint.

Still another objective of the invention is to fasten to the bone a construct such as a membrane holding gels, sponges and the like, which may be used to introduce cells and cartilage growth enhancing factors.

SUMMARY OF THE INVENTION

The invention relates to the repair of articulating joints by forming a gap between at least part of the articulating surfaces of two bones in the joint. The gap is maintained for a period of time while cells grow into the gap on the articulating surface of at least one bone. The cells are protected during growth, typically by shields and/or spacers. Preferably the growing cells form cartilaginous tissue on the articulating surface which protects the joint from further damage. The joint can remain mobile during cell growth. The removal of at least some of the cartilage from the articulating surface from the joint to the bleeding subchondral bone is preferred.

The invention also relates to the repair of articulating joints using prosthetic shields and spacers in order to keep the bones of the joint separated. In one embodiment of the invention, the shield is a curved trough shaped to extend along at least a portion of the articulating surface of a first bone of the joint. The trough has inner and outer surfaces and opposite ends. A spacer head receiving groove is located in the outer surface of the trough and preferably extends from one end to the other. A spacer can be located on a second bone opposite the trough, with the spacer head fitting within the groove.

Alternatively, the shield can be a cap. The cap has a concave inner surface and a convex outer surface and is shaped to fit at least a portion of the articulating surface of a first bone of the joint. When the cap is placed over the bone, a gap forms between at least a part of the concave surface of the cap and the bone's surface. The cap may have a fastener with a fastener shaft and means for separating the fastener and the inner concave surface.

Additional effects, features and advantages will be apparent in the written description that follows.

DETAILED DESCRIPTION OF THE INVENTION

Several aspects of the invention are described in the figures. To aid in understanding the invention, several figures show the invention in situ with the joints separated.

Figure 1:
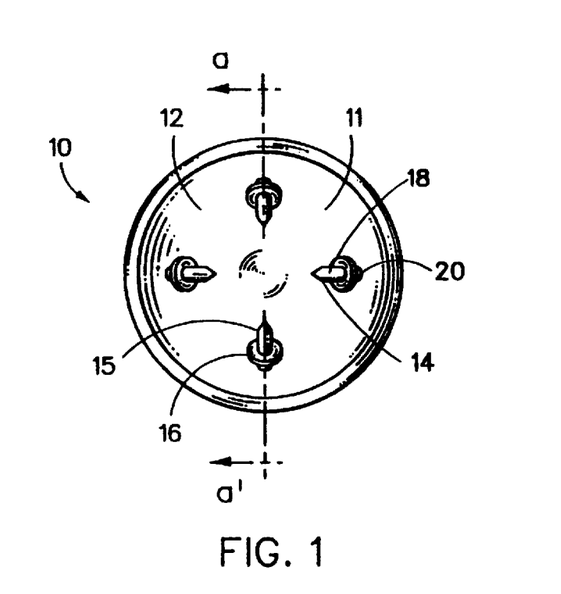
FIG. 1 is a plan view of a shield of the invention.
Figure 2:
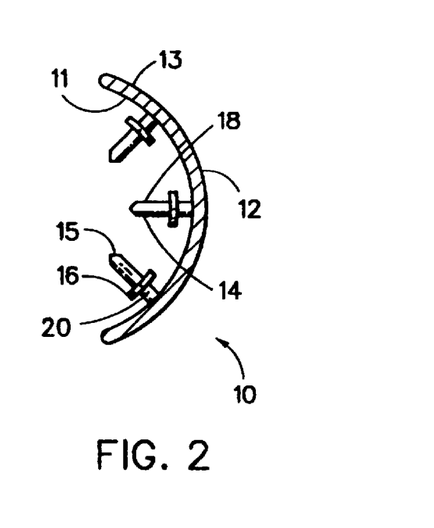
FIG. 2 is a cross-sectional view along lines a–a' of a shield of the invention.
Figure 3:
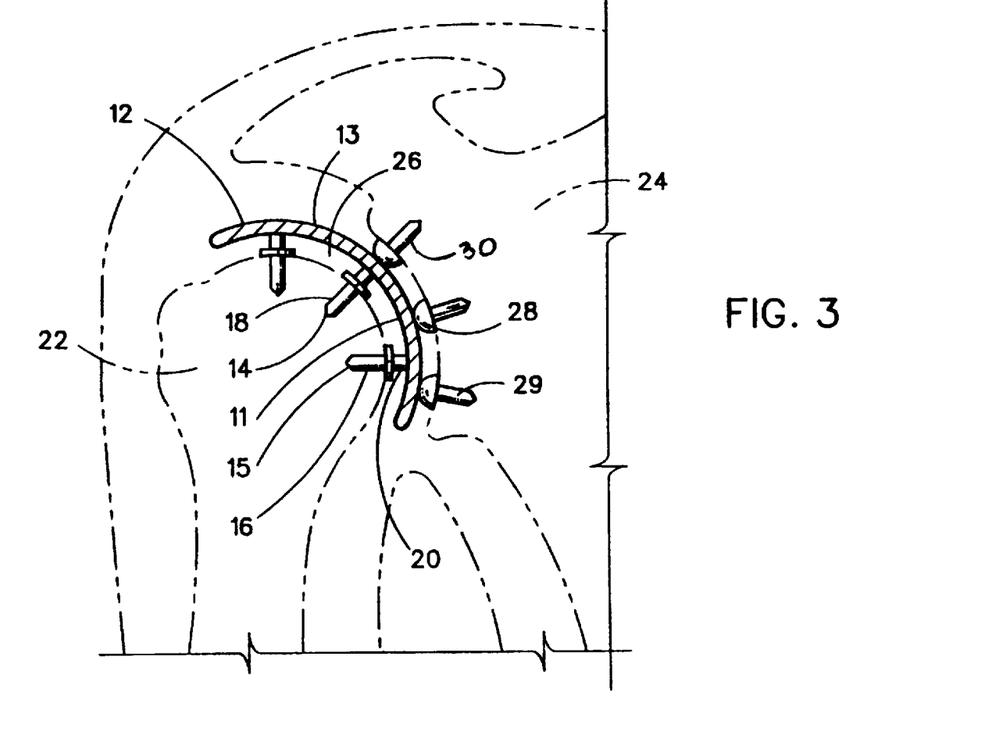
FIG. 3 is a cross-sectional view of a shoulder using a shield of the invention.

FIGS. 1, 2 and 3 show shield 10 of the invention that fits over a bone of an articulating joint, such as the ball of a ball and socket joint. Shield 10 is shaped and sized to conform to the end of the bone. Cap 12 has a concave interior surface 11 and convex exterior surface 13. Cap 12 is typically secured to the bone using fasteners 14, 15, such as screws, pins, pegs, and the like. Fastener 14 has shaft 18 which can have flexible flanges, serrations, threads, pins or slots to facilitate implantation by any method, such as press-fitting, screwing or driving into the bone with a mallet. Head 16 is preferably part of the fastener and is typically flat. Alternatively, head 16 may be a disc, ring, band or grommet attached to and/or encircling the fastener shaft between the bone and the cap. When part of the fastener, head 16 stops the fastener at a desired distance within the bone. Usually a stem 20 is located between head 16 and cap 12 and is preferably part of the fastener. Heads or stems separate at least a portion of the concave surface of the cap from the bone. Heads, stems and the cap are typically smooth, although they may be textured or chemically treated to enhance the regrowth of articular cartilage, such as by providing a site for cellular attachment.

Referring to the shoulder shown in FIG. 3, the head of the humerus 22 has shield 10 implanted opposite the glenoid of scapula 24. Shield 10 covers humeral head 22 and has strew-type fasteners. Stem 20 separates humeral head 22 from cap 12 to form gap 26.

Preferably, a plurality of spacers is disposed between the articulating surfaces as described in U.S. Pat. No. 5,108,441 issued to Charles L. McDowell, which is incorporated herein in its entirety by reference. Spacers 28, 29, 30 are implanted in the glenoid of scapula 24 opposite humeral head 22. Preferably spacers 28, 29, 30 are arranged equidistant in glenoid 24 to form a "pocket" to receive the shielded humeral head 22. More preferably spacers 28, 29, 30 are arranged in glenoid 24 to create a tripod "pocket" to seat the round shield 10 implanted in humeral head 22. Alternatively, spacers could be used without implanting a shield on the opposite bone as described in '441.

Shield 10 and spacers 28, 29, 30 keep the articulating surfaces of the joint separated. This facilitates the regeneration of articular cartilage between the articulating surfaces in the shoulder joint by protecting the surface of the humeral head from rubbing against the spacers or opposite bone.

Although the preferred embodiment of the shield is shown fully assembled with cap, fasteners and stems in place, the shield can be part of a kit where the individual parts are assembled before or during surgery. Stems and heads can be individual components, part of the fastener or attached to the cap.

Figure 4:
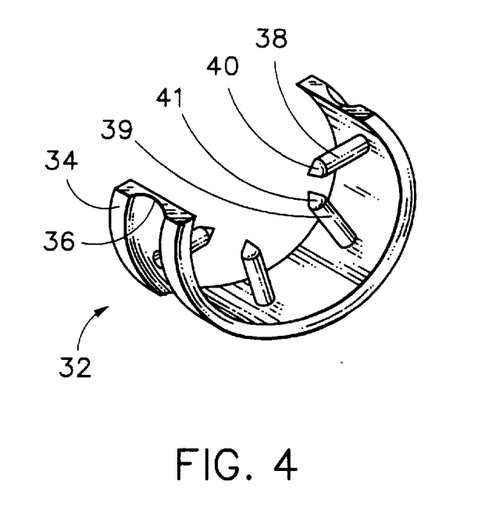
FIG. 4 is a perspective view of a shield of the invention rotated from lateral to the posterior position.

Another form of the invention shields hinge joints, such as the knee, elbow or finger as shown in FIG. 4. For hinge joints, shield 32 has trough 34 with spacer head receiving groove 36. Trough 34 extends over at least a portion of the articulating surface of the bone of the joint, such as the condyle of the femur or the head of a metacarpal or phalanx. The trough is designed to fit the shape of the bone of the chosen joint, for example, a femoral condyle. A spacer head receiving groove 36 is in the outer surface of the trough and preferably extends from one end of the trough to the other.

Trough 34 implants to the bone with fasteners 38, 39. Fasteners 38, 39 have fastener shafts 40, 41 which can have flexible flanges, pins, threads, serrations or slots and are implanted by any method, such as press-fitting, screwing or driving into the bone with a mallet. If desired, a head, such as a fastener head, or a disc, ring, band or grommet attached to and/or encircling the fastener shaft between the bone and the trough can be used. The head can separate the inner surface of the trough from at least a portion of the articulating surface of the bone. Although the entire shield is shown fully assembled with a trough and fasteners in FIG. 4, the shield can be part of a kit where the fasteners, heads and the trough are separate pieces assembled before or during surgery.

Figure 5:
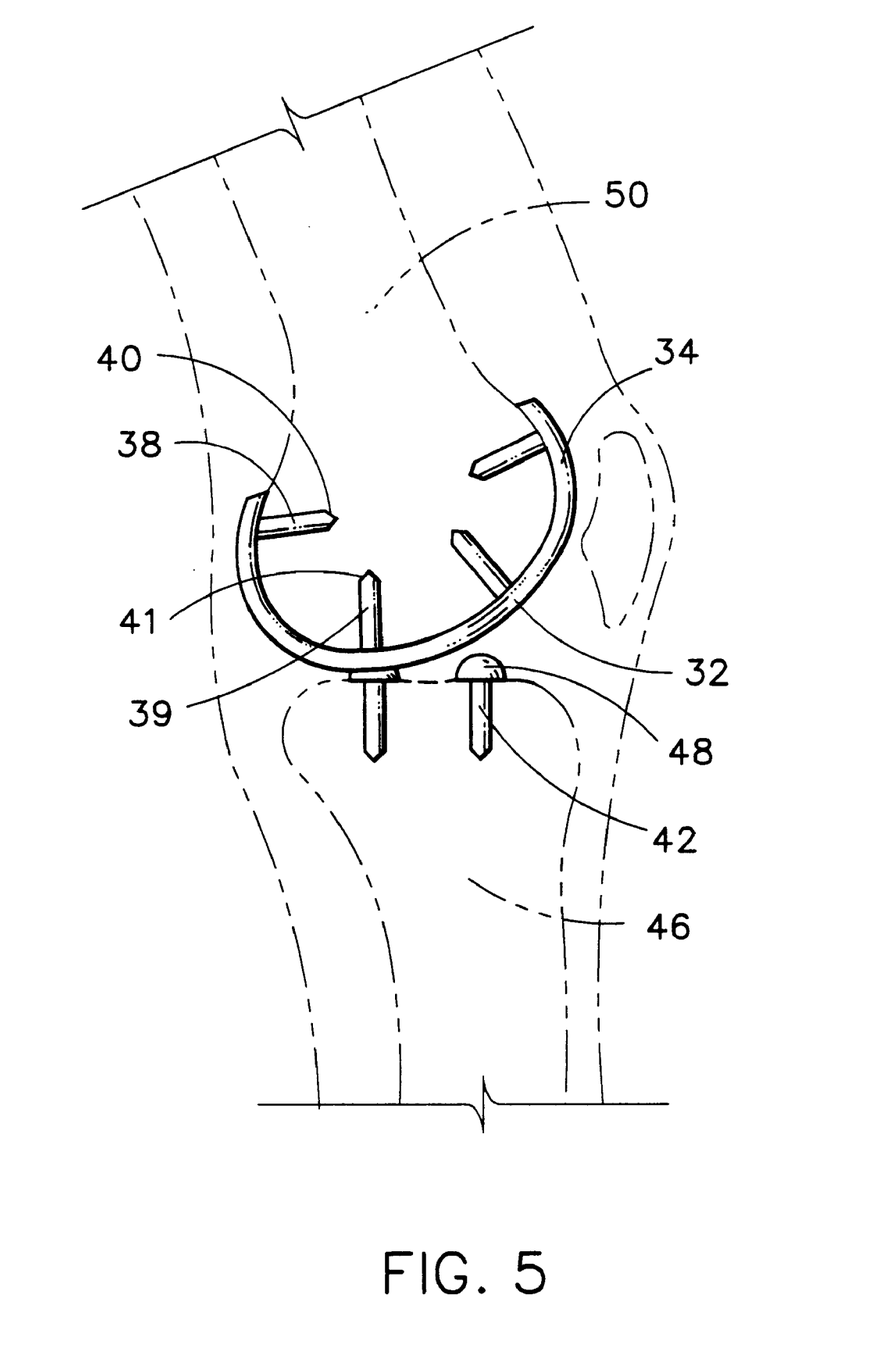
FIG. 5 is a lateral view of a knee using a shield of the invention.
Figure 6:
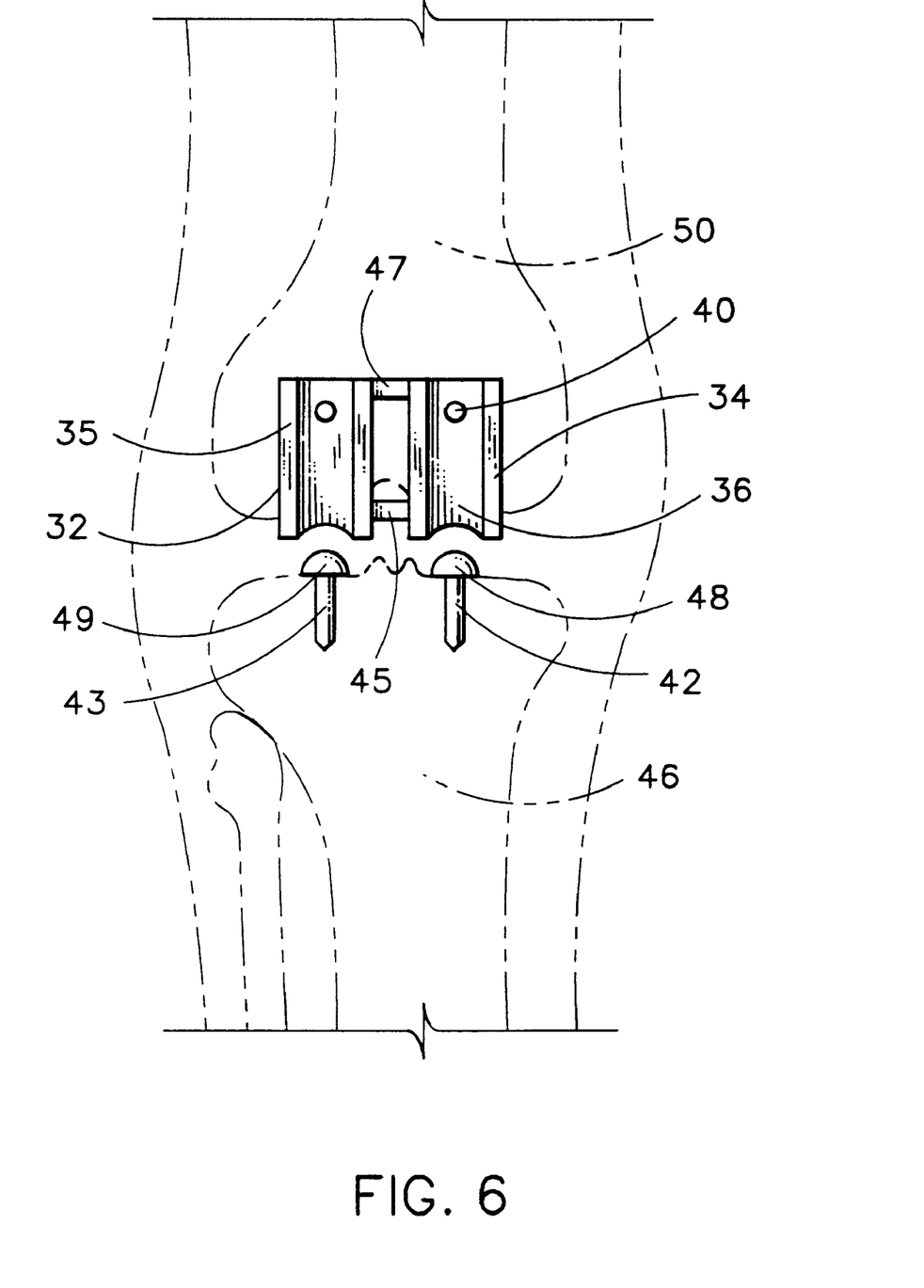
FIG. 6 is a posterior view of a knee with a shield of the invention.

FIGS. 5 and 6 show the shield of the invention implanted in a large hinge joint. In a knee, spacers 42, 43 are implanted in the condyles of the tibia 46, preferably near the tubercles of intercondylar eminence. Spacers 42, 43 have heads 48, 49 that extend from the bone. Spacer heads 48, 49 are preferably domed. Troughs 34, 35 are implanted on the condyles of the femur 50 opposite spacers 42, 43. Trough 34 is oriented so that groove 36 receives spacer head 48. Similarly, trough 35 is oriented so that groove 37 receives spacer head 49 and is parallel to trough 34. Troughs 34, 35 extend around the articulating surface of the condyles of the femur 50 and cup the condyles. When the hinge joint moves, the spacer head tracks within the groove. Preferably, troughs 34, 35 are interconnected, for example, an anterior bridge and posterior bridge 47 positioned between the troughs to preserve their proper alignment within the joint. If desired, additional interconnections such as a medial bridge 45 may also be used to preserve the alignment of the troughs within the joint.

Figure 7:
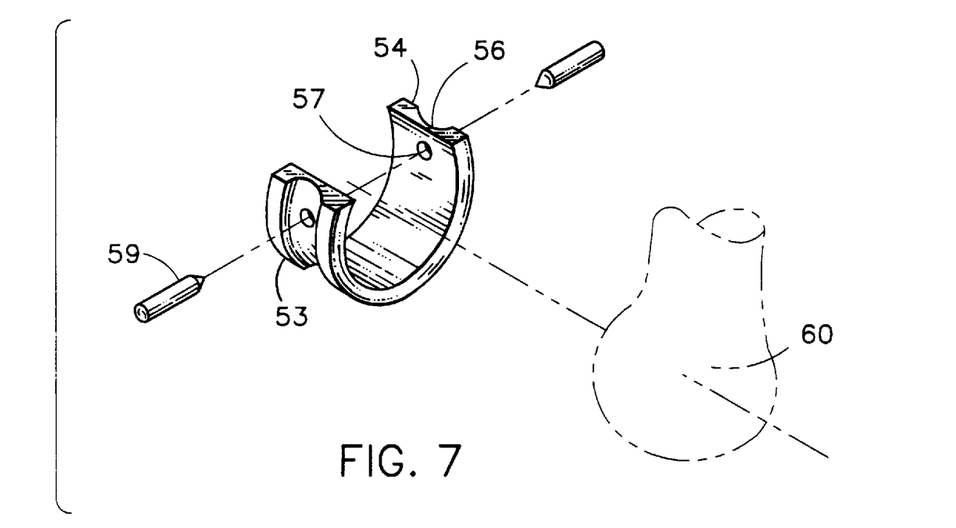
FIG. 7 is an exploded perspective view of a bone with a shield of the invention.
Figure 8:
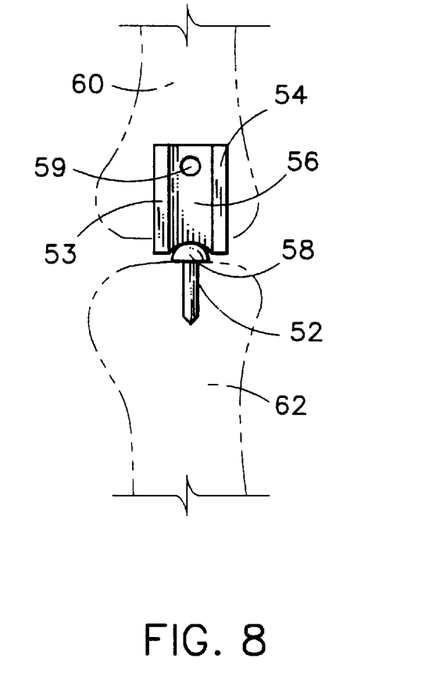
FIG. 8 is a plan view of a finger with a shield of the invention.

Small hinge joints can use the shield and a spacer similarly to that described for the knee. FIGS. 7 and 8 show a finger with spacer 52 implanted in the base of phalanx 62. Shield 53 implants on the head of the metacarpal 60 opposite spacer 52. Trough 54 is oriented so that groove 56 receives spacer head 58. Trough 54 extends around the articulating surface of the metacarpal head 60. When the hinge joint moves, the spacer head tracks within the groove. If desired, shield 53 may have fastener opening 57, such as a bore, to receive fastener 59.

In one method of the invention, after first separating the bones of the articulating joint, a gap forms between at least a portion of the articulating surfaces of the bones of the joint. The bone is at least partially denuded or abraded to remove damaged bone and tissue. Preferably, the abrasion is to the bleeding subchondral bone.

Typically, the gap forms between a shield and the first bone of the joint. The shield can be implanted with fastener shafts in the bone. The bone may also be prepared by making fastener receiving openings for the fastener shafts, such as by drilling, and inserting the fastener shafts into the fastener receiving openings. Preferably, the shield is located opposite spacers implanted in the opposing second joint bone.

When the shield is a cap with fasteners and stems as one integral piece, the shield is implanted into the bone by any known method, such as by using self driving fasteners with flexible flanges that can be press-fitted into place. If the cap contains stems, the stems are seated onto the heads of the fasteners and are affixed in place by any medically approved method, such as cementing. Alternatively, the fasteners may have the stems already attached and the cap is seated onto the stems or directly onto the heads. The cap is preferably affixed to the stems or heads by any medically approved method. The socket bone of the socket joint preferably has spacers implanted, more preferably the spacers are implanted at equidistant intervals to form a "pocket" to receive the shielded head of the ball of the joint. Most preferably the spacers are positioned to form a tripod "pocket" to seat the shielded head.

When the shield is attached to a bone within a hinge joint, the shield has a trough. The trough has a groove to receive the head of a spacer implanted in the opposite bone of the joint. The trough extends along at least a portion of the articulating surface of the bone and is designed to fit the bone into which it is implanted. The trough is preferably held in place by fasteners which are preferably connected to the trough. If the joint is large, such as the knee, two parallel troughs are used as the shield and are preferably interconnected together at the ends. Each groove of each trough receives at least one spacer head of a spacer implanted in the opposite bone.

The shield of the invention is made from any medically approved material which has some rigidity and does not collapse under the stresses present in the joint over time. Suitable materials include metals, such as titanium and stainless steel, and organic polymers, for example, high density polyethylene, ultrahigh density polypropylene, polymeric polylactic acid, and the like, and their copolymers and combinations thereof. If desired to enhance cell growth and cartilage production, the shield and spacers can be chemically treated.

During surgery, cartilage producing stem cells can be accessed by removing all damaged cartilage or scar tissue from the bone surface. Preferably, the bone surface is denuded by removing bone tissue to the bleeding subchondral bone, such as by abrasion.

After surgery, tissue growth can be monitored by periodically assessing tissue formation or tissue growth and/or repair by methods known in the art, for example, X-rays, arthroscopy, histomorphometric determinations, nuclear magnetic resonance and tetracycline labeling.

Stem cells can be transplanted to the site, for example, by grafting on the surface of the bone or by grafting to the bleeding subchondral bone. Cells could also be attached to the shield or spacers themselves before implantation, where the shield and spacers serve as an anchor or scaffold to which the cells attach. The cells can be transplanted from other parts of the body (autografts), transplanted from another donor (heterografts or xenografts) or harvested from in vitro cell cultures. Cells can include isolated periosteal cells, mesenchymal stem cells or chondrocytes.

Cells can also be transplanted to the joint in a construct such as a gel or sponge which are then covered by a membrane to protect the cells from dispersal until the cells attach. The membrane can be secured to the edge of the joint by suturing, fibrin glue, and the like. Holes can then be drilled into the membrane when drilling holes into the bone for the fastener shafts and spacer shafts. Alternatively, the membrane could be punctured when driving the fastener and spacers shafts into the bone. The shield and spacers hold the membrane in position on the joint as well as shield it and the transplanted cells from compressive and frictional stresses. The membranes are well known in the art and can be made of any medically approved materials.

New tissue growth can be enhanced by using a substrate, such as temporary tissue substitutes like donor tissue, synthetic cartilage, for example, biodegradable polymers like SIS, a polymer derived from small intestinal submucosa (available from Purdue University, Warsaw, Indiana and DePuy, Inc., Warsaw, Ind.), biodegradable sponges, films or other forms of scaffolding. These materials can be made of collagen, hyaluronic acid, polyglycolic acid, polylactic acid, polydioxane, polyester, alginate, reticulin, elastin, cellulosic materials (alkylcelluloses, methylcellulose, ethylcellulose, hydroxyethylcellulose, hydroxypropylcellulose, hydroxypropyl-methylcellulose, carboxymethylcellulose and cationic salts of carboxymethylcellulose), alginate, polyethylene glycol, polyoxyethylene oxide, carboxyvinyl polymer, polyvinyl alcohol, chitosan and their analogs, recombinant forms, bioequivalent variants, copolymers, as well as any combinations thereof. Cells for transplant may also be inserted into this substrate material.

New tissue growth may also be enhanced by the delivery of growth promoting and/or attachment factors, such as growth factors, fibroblast growth factor (acidic or basic), transforming growth factor beta (TGF-β 1, 2 or 3, one of the members of the superfamily of proteins of TGF-β, such as bone morphogenetic proteins, BMP), parathyroid hormone related polypeptide (PTHrP) or an equivalent PTH-like polypeptide, insulin, insulin-like growth factors (IGF-I and IGF-II), platelet-derived growth factors (PDGF), epidermal growth factor (EGF), transforming growth factor-α (TGF-α), activins, inhibins, fibroblast growth factor-4 (FGF-4), parathyroid hormone (PTH), leukemia inhibitory factor (LIF/HILDA/DIA), and the like, as well as their analogs, recombinant forms, bioequivalent variants, copolymers, or combinations thereof. The attachment factors which can be used include fibronectin, RGD polypeptide, and the like, as well as their analogs, recombinant forms, bioequivalent variants, copolymers or combinations thereof Attachment and/or growth factors can be delivered to the site via the shield and spacers. The shields and spacers can be impregnated with these factors during their manufacture, such as during polymerization, or added after manufacture, such as by bonding or crosslinking. The factors may also be encapsulated or similarly treated for their slow release into the site. The shields and spacers can also deliver or fasten to the site a matrix impregnated with attachment and growth factors, such as biodegradable sponges, mesh, fibrin clot, collagen gel, cartilage or other types of biological scaffolding materials made of collagen, hyaluronic acid, polyglycolic acid, polylactic acid, isolated periosteal cells, polydioxane, polyester, alginate, and the like, as well as their analogs or combinations thereof. The matrix can in turn be covered by the membrane described above.

After cells have grown on the articulating surface between the joints to form new tissue such as cartilage-like tissue, the shields and spacers may be removed. If biodegradable materials are used, the material degenerates over time. The removal of the shield and spacers leaves a completely natural joint in which the damaged cartilage between bones has been replaced by new healthy tissue.

EXAMPLE

A canine patello-femoral joint was used as an in vivo model. Articular cartilage was removed to the bleeding subchondral bone from the patellar side of the joint of twelve skeletally mature, mongrel dogs, each dog about 25 kg. A medial parapatellar incision was made into the knee joint of both hindlimbs. The two patellae were everted, and all of the articular cartilage and a thin layer of subchondral bone were removed using a high speed burr leaving a uniform surface of bleeding subchondral bone.

Two dome-shaped polyethylene spacers were implanted into 3.5 mm holes drilled into the cortices of the bone at the proximal and distal poles of one patella to protect the patellar surface from contact with the patello-femoral groove in the manner described in the '441 patent to form a gap between the patella and femur. The spacer head protruded into the gap about 3 mm. No spacers were implanted into the other patella. Incisions were closed in standard fashion and the dogs were permitted ad libitum pen activity until the time of euthanasia at 6 or 12 weeks post surgery.

The neocartilage from the patellae and the patello-femoral grooves was evaluated through gross visualization, histological evaluation, biomechanical and biochemical quantification. The normal baseline of cartilage characteristics was determined by performing the same evaluations on patella-femoral grooves from dogs without joint surgery. Assessing the grooves determined the extent, if any, of damage to this surface. The proximal two thirds portion of the patellae was quantified biomechanically and biochemically, while the remaining distal portion was evaluated histologically.

At all angles of flexion tested, the only contact made between the patella and the patella-femoral groove were at the sites of the implanted spacer. At maximum extension, the distal spacer was the point predominantly in contact with the groove while with increasing flexion, the point of contact moved proximally. Stress relief was confirmed visually as the separation between the two surfaces was evident from both superior and lateral views.

After 6 and 12 weeks, the experimental knees (N=6 at each time point) had new tissue growth that completely surrounded the implanted spacers on the patellar surface. The thickness of the new tissue was equivalent to the height of the spacers (3 mm). The control specimens (N=6 at each time point) showed no such new tissue growth on the cartilage denuded articular surface where subchondral bone was in contact with the contralateral normal cartilage surface. The control specimens had minimal growth of new tissue at isolated sites along the edges where the denuded surface was not in contact with the contralateral normal cartilage surface. In no control specimen, however, did the new growth rival the new growth on the experimental surface.

At 6 weeks, the gross and histological appearance of the repair tissue showed a thick repair tissue covering at least about 75% of the surface of the patellae. By 12 weeks, coverage increased to greater than about 75%. The control patellae showed about 0% to about 50% repair tissue coverage of the patella in areas where there was no mechanical stress shielding. The control tissue growth varied in thickness from about 0% where the subchondral bone was exposed to a maximum of about 50% of normal thickness in the twelve weeks specimens. Surface quality was graded irregular. Shallow clefts were noted in the experimental tissue while clefts to the tide mark and exposed bone were evident in all of the control specimens.

The quality of the newly grown tissue improved in appearance from the 6 to 12 week specimens. Cell morphology in the new tissue was characterized largely as fibrocartilage in all specimens, although the experimental patellae had some areas of newly differentiated chondrocytes.

The hyaline cartilage in the femoral groove was examined to evaluate the extent of damage produced by contact with the implanted polyethylene spacers. Some damage to the hyaline cartilage in the femoral groove occurred between 6 and 12 weeks in the experimental specimens. This damage was suggested by a 50% loss of cartilage thickness, as well as chondrocyte clustering and hypocellularity. At 6 weeks the damage was worse in the control specimens while at 12 weeks it was worse in the experimental specimens. This indicates that the spacers were well tolerated for at least about 6 weeks.

Biomechanical results indicated that new growth on the experimental patellae had a lower modulus and greater permeability than normal patellar hyaline cartilage. The modulus for cartilage from the experimental patellae was significantly less than that for normal tissue ($p<0.001$) but not different between 6 and 12 weeks. Thickness of new growth measured using indentation testing under a constant load measuring the compressive deformation (creep) was an average of $1.62\pm0.51$ mm at the side of indentation, while the normal patellae from the control (nonsurgical) group was $0.67\pm0.26$ mm. The grooves for the two groups were similar, thus suggesting the experimental grooves were not damaged by the spacers.

Biochemically, the experimental patellae had increased hydration of the cartilage versus the normal control joints (80.6±3.1% at 6 weeks and 78.0±1.6% at 12 weeks 63.9±10.0 (N=3) for the control). Hydration in the grooves was within normal limits for the experimental group.

This study confirms that completely denuding a joint surface down to a level of bleeding subchondral bone allows new tissue to grow to completely cover the subchondral bone only if the surface is shielded from the mechanical effects of compression and shear by the opposing joint surface.

The shields, spacers and the methods of their usage of the invention have a number of advantages. The combination of shields and spacers separates and cushions the joints. Like articulating cartilage, shields and spacers protect the bone from damage caused by compression and friction. The groove of the shield, for example, smoothly allows the spacer head to glide in the groove during movement to reduce friction.

Another advantage of the invention is the production of new tissue on the articulating surface. Removing damaged or surface tissue down to the bleeding subchondral bone accesses healthy stem cells or cartilage-producing cells, such as endothelial cells, fibroblasts or chondrocytes. Because the invention protects growing cells by reducing compressive and frictional stresses, the cells grow out of the interior of the bone and onto the protected surface of the joint. These healthy stem cells can grow into the gap between the shield and bone and produce cartilage-like tissue.

Another advantage of the method of the invention is that new cell growth is integral with the bone. If the surface is denuded to the bleeding subchondral bone, the new cells grow from the bone surface and form cartilage-like tissue. This new cartilage-like tissue will not separate from the bone, so there is no problem with attachment to the bone nor adjacent tissue as seen with other techniques. Additionally, the bleeding subchondral bone provides a rich surface for transplanted cells to attach and grow. The bleeding subchondral bone also provides access to the body's own wound repairing mechanisms and natural growth factors involved in tissue regeneration, such as platelet derived growth factors.

Still another advantage of the invention is that repair occurs over a larger portion of the articulating surface. Because a larger surface is shielded, the new tissue can grow over this larger surface, and thus repair more of the articulating surface.

The shields and spacers of the invention also provide a platform to which tissue-producing materials attach. Whether in vivo or in vitro transplants, stem cells, for example, fibroblasts, chondroblasts, fetal tissue, periosteum and endothelial cells can attach and grow onto the shield. Therefore, artificial cartilaginous-like materials, stem cells, attachment factors, growth factors and the like can be attached to the shield and spacers before implantation and delivered to the joint. In addition, the shield and spacers can attach and protect scaffolding material that is impregnated with stem cells, attachment factors and growth factors to the joint. Similarly, the shield and spacers can attach and protect membranes covering a construct, such as a fibrin gel or a sponge, that is impregnated with stem cells, attachment factors and growth factors to the joint.

While the invention is shown in only one of its forms, it is not thus limited but is susceptible to various changes and modifications without departing from the spirit and scope of the invention.

What is claimed is:

1. A method of repairing a joint having an articulating surface, the method comprising the steps of:

forming a gap between at least part of the articulating surfaces of two bones in the joint;

denuding to the bleeding subchondral bone at least a portion of the articulating surface of one bone of the joint;

maintaining the gap for a period of time;

allowing cells to grow into the gap on the articulating surface of at least one bone;

implanting a shield into a first bone of the joint at the articulating surface;

implanting a spacer into a second bone of the joint at the articulating surface opposite the first bone; and protecting the cells growing on the articulating surface of at least one bone.

2. The method of claim 1, further comprising the step of:

denuding to the bleeding subchondral bone at least a portion of the articulating surfice of another bone in the joint.

3. The method of claim 1, further comprising the step of:

treating the denuded portion of the articulating surface to enhance cell growth.

4. The method of claim 3, wherein the denuded portion is treated by exposing the denuded portion to a factor selected from the group consisting of growth factors, attachment factors, recombinant growth factors, recombinant attachment factors, growth factor analogs, attachment factor analogs, and combinations thereof.

5. The method of claim 1, further comprising the step of:

transplanting cells to the denuded articulating surface.

6. The method of claim 1, further comprising the step of:

placing a substrate onto the denuded articulating surface.

7. A method of repairing a joint having an articulating surface, the method comprising the steps of:

forming a gap between at least part of the articulating surfaces of two bones in the joint;

denuding to the bleeding subchondral bone at least a portion of the articulating surface of one bone of the joint;

maintaining the gap for a period of time;

transplanting cells to the denuded articulating surface;

covering the transplanted cells with a membrane;

securing the membrane with a spacer;

allowing cells to grow into the gap on the articulating surface of at least one bone; and protecting the cells growing on the articulating surface of at least one bone.

8. A method of repairing a joint having an articulating surface, the method comprising the steps of:

forming a gap between at least part of the articulating surfaces of two bones in the joint;

denuding to the bleeding subchondral bone at least a portion of the articulating surface of one bone of the joint;

maintaining the gap for a period of time;

transplanting cells to the denuded articulating surface;

covering the transplanted cells with a membrane;

securing the membrane with a shield;

allowing cells to grow into the gap on the articulating surface of at least one bone; and protecting the cells growing on the articulating surface of at least one bone.

9. A method of claim 1, further comprising the step of:
using the shield to deliver a factor to the denuded site, wherein the factor is selected from the group consisting of growth factors, attachment factors, recombinant growth factors, recombinant attachment factors, growth factor analogs, attachment factor analogs, and combinations thereof.

10. A method of claim 1, further comprising the step of:
using the spacer to deliver a factor to the denuded site, wherein the factor is selected from the group consisting of growth factors, attachment factors, recombinant growth factors, recombinant attachment factors, growth factor analogs, attachment factor analogs, and combinations thereof.

11. The method of claim 6, wherein the substrate is impregnated with a factor selected from the group consisting of growth factors, attachment factors, recombinant growth factors, recombinant attachment factors, growth factor analogs, attachment factor analogs, and combinations thereof.

12. A method of claim 7, further comprising the step of:
using the spacer to deliver a factor to the denuded site, wherein the factor is selected from the group consisting of growth factors, attachment factors, recombinant growth factors, recombinant attachment factors, growth factor analogs, attachment factor analogs, and combinations thereof.

13. A method of claim 8, further comprising the step of:
using the shield to deliver a factor to the denuded site, wherein the factor is selected from the group consisting of growth factors, attachment factors, recombinant growth factors, recombinant attachment factors, growth factor analogs, attachment factor analogs, and combinations thereof.

* * * * *